US00PP31663P2

(12) United States Plant Patent
Ronald

(10) Patent No.: US PP31,663 P2
(45) Date of Patent: Apr. 14, 2020

(54) ***DASIPHORA* PLANT NAMED 'JEFMARM'**

(50) Latin Name: ***Dasiphora fruticosa* subsp. *fruiticosa***
Varietal Denomination: Jefmarm

(71) Applicant: Jeffries Nurseries Ltd, Portage la Prairie (CA)

(72) Inventor: Wilbert Ronald, Portage la Prairie (CA)

(73) Assignee: JEFFRIES NURSERIES, LTD, Portage la Prairie (CA)

( * ) Notice: Subject to any disclaimer, the term of this patent is extended or adjusted under 35 U.S.C. 154(b) by 0 days.

(21) Appl. No.: 16/501,239

(22) Filed: Mar. 11, 2019

(51) Int. Cl.
*A01H 5/02* (2018.01)
*A01H 6/74* (2018.01)

(52) U.S. Cl.
USPC ..... Plt./237
CPC ..... *A01H 6/74* (2018.05)

(58) Field of Classification Search
USPC ..... Plt./237
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Dasiphora*, 'Jefmarm', that is characterized by its double flowers that are yellow with a distinct orange-red tinge, its flowers that fade in hot weather to a dark yellow color, and its extended blooming period.

2 Drawing Sheets

Botanical classification: *Dasiphora fruticosa* subsp. *fruiticosa.*

Variety denomination: 'Jefmarm'.

BACKGROUND OF THE INVENTION

The present invention relates to a new and distinct cultivar of *Dasiphora fruticosa* subsp. *fruiticosa* (syn. *Dasiphora fruticosa*). The new cultivar will be referred to hereafter by its cultivar name, 'Jefmarm'. 'Jefmarm' is a new cultivar of deciduous shrub grown for landscape use.

The new cultivar arose from a cross made by the Inventor in Portage La Prairie, Manitoba, Canada in 2012 between 'Uman' (U.S. Plant Pat. No. 12,258) as the female parent and 'Marrob' as the male parent (not patented). The Inventor selected 'Jefmarm' as a single unique plant amongst the seedlings that resulted from the above cross in 2013.

Asexual propagation of the new cultivar was first accomplished by softwood cuttings under the direction of the Inventor in Portage La Prairie, Manitoba, Canada in spring of 2014. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub. These attributes in combination distinguish 'Jefmarm' as a unique cultivar of *Dasiphora.*

1. 'Jefmarm' exhibits double flowers that are yellow with a distinct orange-red tinge.
2. 'Jefmarm' exhibits flowers that fade in hot weather to a dark yellow color.
3. 'Jefmarm' exhibits an extended blooming period.

The seed parent of 'Jefmarm', 'Uman', differs from 'Jefmarm' in having smaller single flowers that are less red in color, and in being less floriferous. The pollen parent of 'Jefmarm', 'Marrob', differs from 'Jefmarm' in having poorer viability and poorer foliage health when grown in U.S.D.A. Zones 3 to 5 and in prairie soils of Midwest regions of the U.S. 'Jefmarm' can also be compared to the cultivar 'Jefman' (U.S. Plant Pat. No. 29,830). 'Jefman' is similar to 'Jefmarm' in flower color and plant habit. 'Jefman' differs from 'Jefmarm' in having single flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to website listings by bylands.com, jeffriesnurseries.com, marketwatchplants.com, issuu.com, and firsteditionsplants.com.

BRIEF DESCRIPTION OF THE DRAWINGS

The accompanying colored photographs illustrate the overall appearance and distinct characteristics of the new *Dasiphora*. The photographs were taken of a 3-year-old plant as grown outdoors in a 2-gallon container at a nursery in Portage la Prairie, Manitoba, Canada.

The photograph in FIG. 1 provides a view of a plant of 'Jefmarn' in bloom.

Figure 1:
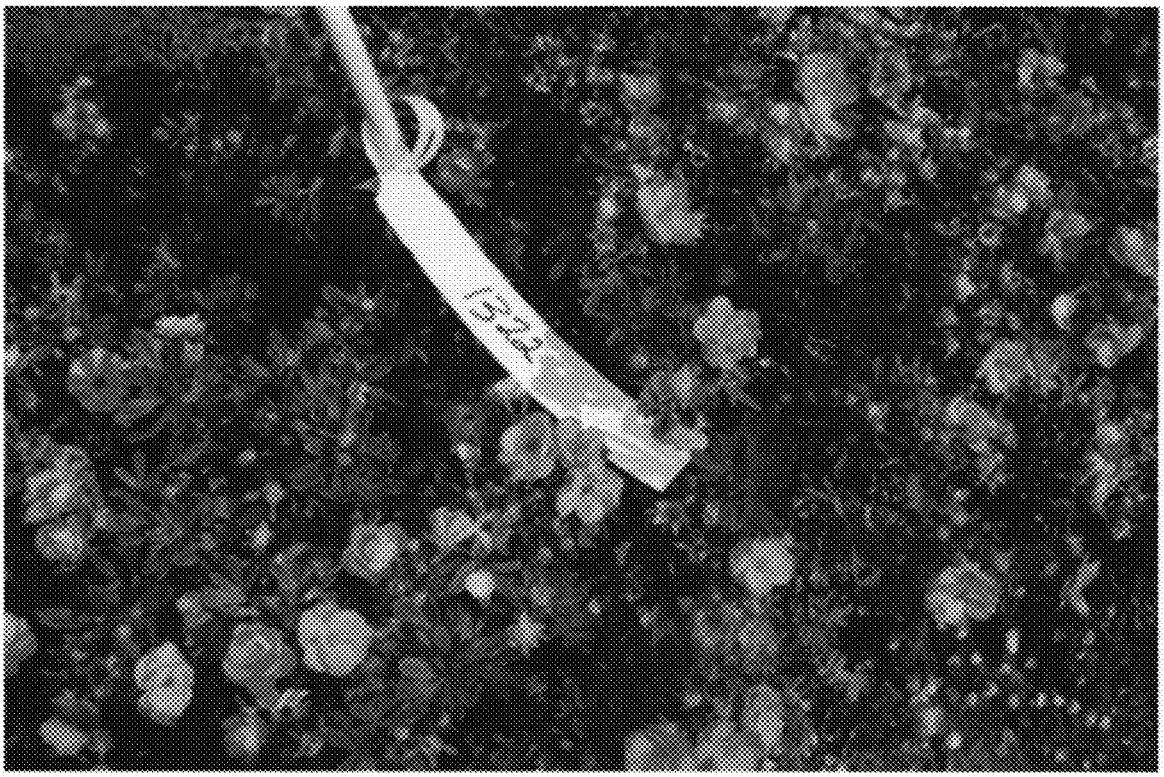
Figure 2:
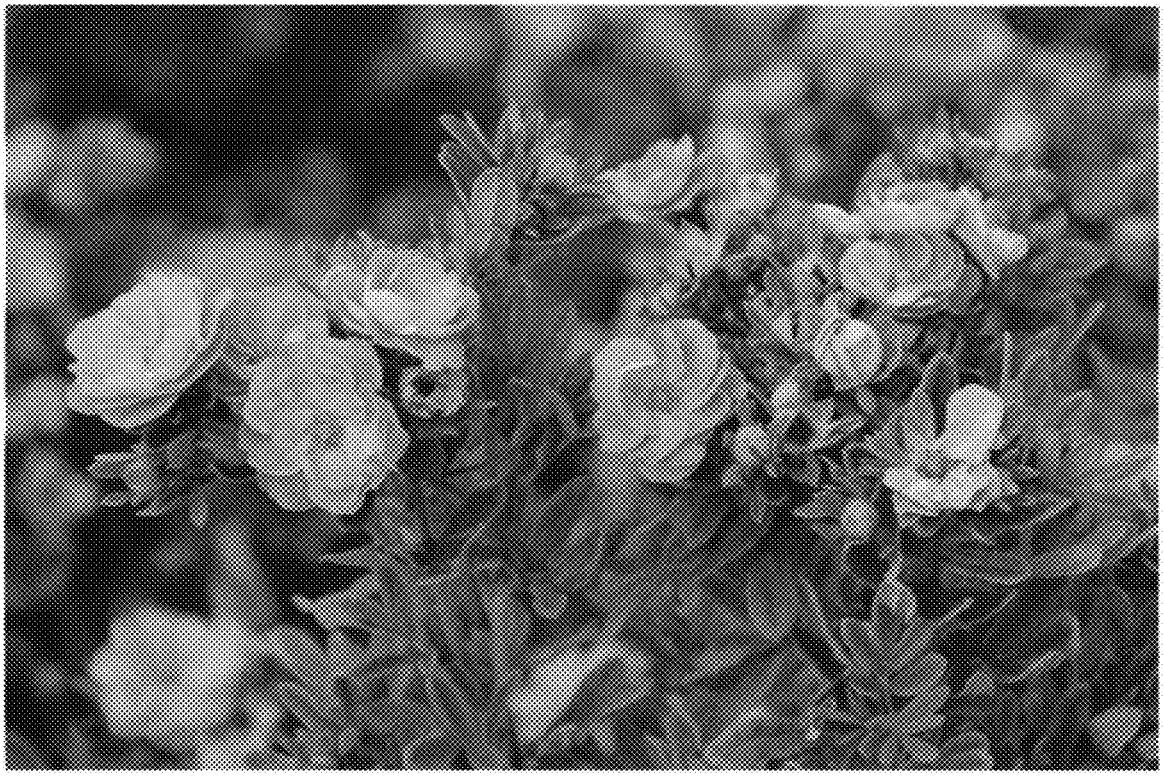

The photograph in FIG. 2 provides a close-up view of the flowers of 'Jefmarn'.

The colors in the photographs are as close as possible with the photographic and printing technology utilized and the color values cited in the detailed botanical description accurately describe the colors of the new *Dasiphora.*

DETAILED BOTANICAL DESCRIPTION

The following is a description of 3-year-old plants as grown outdoors in two-gallon containers in Portage la Prairie, Manitoba, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Long blooming period; July 1 to September 30 in Canada.

*Plant type*.—Deciduous shrub.

*Plant habit*.—Upright and bushy.

*Height and spread*.—An average of 90 cm in height and width as a mature plant in the landscape.

*Hardiness*.—At least in U.S.D.A. Zones 2 to 6.

*Diseases and pests*.—Has shown good disease resistance but causative agents of resistance have not been identified, no specific susceptibility or resistance to pests has been observed.

*Propagation*.—Softwood cuttings.

*Root description*.—Fibrous, N170A and 200A.

*Growth rate*.—Moderate.

*Root development*.—Cuttings initiate roots in about 2 weeks and a fully rooted cutting is produced in about 6 weeks.

Branch description:

*Branch shape*.—Rounded.

*Branch color*.—Young; 145A, mature wood; 175A and N199A and 200A.

*Branch surface texture*.—Heavily pubescent, rough, rugose and woody with age.

*Branching*.—Freely branching, regular, upright to spreading, medium strength.

*Branch size*.—An average of 48 cm in length and 6 mm in diameter.

*Branch quantity*.—An average of 25 lateral branches.

*Internode length*.—Average of 5 mm.

Foliage description:

*Leaves*.—Compound, odd-pinnate division, alternate arrangement, triangular in shape, an average of 4.5 cm in length and 4.5 cm in width.

*Leaflets*.—5, narrow elliptic in shape, acute to bluntly acute apex, cuneate base, entire margins, color 146A on upper surface and 146B on lower surface, both surfaces dull and glabrous, veins; pinnate and inconspicuous, terminal leaflet an average of 2 cm in length and 5 mm in width, central leaflets; 2 cm in length and 5 mm in width, basal leaflets; 2 cm in length and 5 mm in width.

*Stipules*.—Elliptic to lanceolate in shape, an average of 4 mm in length and 1.5 mm in width, color upper and lower surface; matches stem surface color, upper and lower surface is pubescent, heavily covered with long hairs at base.

*Petioles*.—Petioles; an average of 4 cm in length and 0.5 mm in diameter, moderate strength, color 145A, surface is pilose and slightly glossy, petiolules; none.

Inflorescence description:

*Inflorescence type*.—Solitary, terminal and axillary at upper nodes of stems.

*Flower number*.—An average of 3 to 4 per main stem.

*Flower fragrance*.—None.

*Flower longevity*.—About 5 days, self-cleaning.

*Flower type*.—Double.

*Flower aspect*.—Upwards at an average angle of 45° from horizontal.

*Flower size*.—An average of 2 cm in diameter and 6 mm in depth.

*Peduncles*.—An average of 2 mm in length and 1 mm in diameter, densely pubescent surface with long woolly hairs NN155A in color, surface is 145A in color, strong.

*Pedicels*.—An average of 1 mm in length, 0.5 mm in diameter, densely pubescent surface, 145A in color, medium in strength.

*Flower buds*.—Flattened globose in shape, an average of 7 cm in diameter, 4 mm in depth prior to opening, a blend of 4C and 11A with hints of 13A in color.

*Sepals*.—5, linear in shape, entire margin, color on upper and lowers surface; 146A, an average of 5 mm in length and 1 mm in width, acute apex, cuneate base, both surfaces glabrous, epicalyx; 5-lobed, lanceolate in shape, entire margin, acute apex, an average of 5 mm in length and 3 mm in width, upper and lower surface; 144B in color and both surfaces glabrous and slightly translucent.

*Petals*.—An average of 12 per flower, self-cleaning, oval-rounded in shape, smooth upper and lower surface, margin entire and slightly undulate, cuneate base, rounded apex, an average of 7 mm in length and 5 mm in width, color when opening and fully open upper surface; a blend of 8A and 17A and suffused to varying degrees with 31A to 31B, color when opening and fully open lower surface; 8A and suffused to varying degrees with 31A to 31B, upper and lower surface when grown in hot temperatures typically 13A on upper and lower surface.

*Receptacle*.—Densely pubescent with long translucent shiny hairs NN155A in color, 2 mm in width, 1 mm in depth, 144B in color.

Reproductive organs:

*Pistils*.—Average of 60, en masse 4 mm in diameter, stigma; very minute, rounded in shape and less than 0.5 mm in diameter and 12A in color, style; average of 3 mm in length and <0.5 mm in width, 13B in color, ovary; superior, 3 mm in diameter and depth, and 1D in color.

*Stamens*.—24 per flower, filaments; average of 3 mm in length and 12D in color, anthers; average of 1 mm in length and 0.5 mm in width, ovate in shape, 175A in color, pollen; too minimal in quantity to record color.

*Fruit and seed*.—Have not been observed to date.

It is claimed:

1. A new and distinct cultivar of *Dasiphora* plant named 'Jefmarm' as herein illustrated and described.

* * * * *